United States Patent
Ilmoniemi et al.

(10) Patent No.: US 6,256,531 B1
(45) Date of Patent: Jul. 3, 2001

(54) METHOD AND APPARATUS FOR MAPPING CORTICAL CONNECTIONS

(76) Inventors: Risto Ilmoniemi, Nuottarinne 4 A 2, FIN-02230, Espoo; Jari Karhu, Pajulahdentie 22 A 4, FIN-70260, Kuopip; Jarmo Ruohonen, Vaasankatu 15 C 67, FIN-00500, Helsinki; Juha Virtanen, Sofianlehdonkatu 9 C 25, FIN-00610, Helsinki, all of (FI)

(*) Notice: Subject to any disclaimer, the term of this patent is extended or adjusted under 35 U.S.C. 154(b) by 0 days.

(21) Appl. No.: 09/269,831
(22) PCT Filed: Oct. 30, 1997
(86) PCT No.: PCT/FI97/00664
§ 371 Date: Apr. 1, 1999
§ 102(e) Date: Apr. 1, 1999
(87) PCT Pub. No.: WO98/18384
PCT Pub. Date: May 7, 1998

(30) Foreign Application Priority Data

Oct. 30, 1996 (FI) .......................................... 964387

(51) Int. Cl.⁷ .......................................... A61B 3/00
(52) U.S. Cl. .............................................. 600/544
(58) Field of Search .................... 600/544, 545, 600/300

(56) References Cited

U.S. PATENT DOCUMENTS

| | | |
|---|---|---|
| 4,846,190 | 7/1989 | John . |
| 4,940,453 | 7/1990 | Cadwell . |
| 5,116,304 | 5/1992 | Cadwell . |
| 5,361,773 | * 11/1994 | Ives ........................................ 600/545 |
| 5,730,146 | * 3/1998 | Itil et al. ............................... 600/545 |
| 5,788,648 | * 8/1998 | Nadel .................................... 600/545 |
| 5,797,853 | * 8/1998 | Musha et al. ........................ 600/545 |

FOREIGN PATENT DOCUMENTS 0 504 027    9/1992   (EP) .

* cited by examiner

Primary Examiner—Robert L. Nasser
(74) Attorney, Agent, or Firm—Smith-Hill and Bedell

(57) ABSTRACT

The invention relates to a method and apparatus for examining and mapping the reactivity of and connections between different cortical areas. In the method an electromagnetic stimulus is induced in the interior parts of the head and the electromagnetic field generated around the skull is measured by electrical means (1). According to the method, the electromagnetic activity of the brain is measured using multichannel equipment, artefacts caused by the stimulus are eliminated from the signal containing the electromagnetic activity, a visualization of the activity changes in the measured signals is formed, and the areas of the head related to said activity generating said electromagnetic field are localized, or alternatively, the maximum of the sensitivity pattern of the multichannel activity measurement system is focused to a desired point.

20 Claims, 4 Drawing Sheets

METHOD AND APPARATUS FOR MAPPING CORTICAL CONNECTIONS

The present invention relates to a method for performing brain research of cortical connections and reactivity by virtue of stimulating selected points on the cerebral cortex and, using EEG techniques applied externally to the head, then measuring the distribution of electrical activation evoked by the stimulation.

The invention also concerns an apparatus for research of cortical connections and brain reactivity.

With the help of at least one coil placed on the head, the cerebral cortex can be stimulated without health risks and pain by applying a strong magnetic field, advantageously with a duration of 50–500 µs, that induces an electric current at a desired point. Next, the activated nerve cells transmit along their axons a signal burst to those areas of the brain and peripheral nervous system that have a connection with the stimulated areas. Under the activation, the cells of such areas in turn give rise to electric currents that can be monitored using EEG electrodes placed on the head.

Today, the structure and condition of the brain can be examined by means of CT and MRI imaging equipment, for instance. However, these methods can give information on the condition of cortical connections in very distinct cases only, e.g., when a brain tumor or cerebral infarct has caused damage in the tissue. While EEG and MEG are suited for examination of reactivity of sensory areas to sensory stimuli provided that the peripheral nerve tracts are still functional, the use of these methods in the determination of reactivity to sensory stimuli in other areas of the brain is difficult.

As known from conventional technology, biological tissue and other conductive media can be excited by applying thereon an electromagnetic field composed of an electric field E and a magnetic field B; this fact is utilized in the stimulation of a plurality of different tissues such as the brain, peripheral nervous system and the heart by means of an electric field. Also conventionally, a suitable electromagnetic field can be induced using a coil placed on the object, whereby an alternating electric current fed to the coil induces an alternating magnetic field which further gives rise to an electric field in the object. An alternative method of imposing an electric field on a tissue is to feed current into the organism via electrodes placed on the skin.

As known from conventional techniques, the brain can be stimulated by inducing with the help of a set of coils placed externally to the head, [Ilmoniemi and Grandori 1993, FI Pat. No. 934,511] a strong rapidly changing magnetic field in the brain, whereby the magnetic field induces an electric field in the brain. By virtue of known techniques, the overall effect of the coil set can be focused on an area as small as a few cm$^2$, and using computerized multichannel equipment, the focus of the applied field can be shifted steplessly by altering the relative amplitudes of coil currents in relationship to each other.

Also known in the art are methods in which the electrical activity of the brain is measured in a single-channel system by means of electrodes attached externally to the head, whereby the method is denoted as EEG, or alternatively, directly on the cerebral cortex during an operation, whereby the recording is called an electrocorticogram. The measurement may also be implemented using multichannel equipment, typically comprising 32–128 channels. Then, the electrical activity of the brain can be localized with an accuracy as good as about 5–10 mm.

With modern methods, the electric field used for evoking a response can be inflicted on the brain by subjecting the target area to a magnetic field $B(r,t)$ varying as a function of time t by means of placing a coiled conductor (refer to FIGS. 1a and 2a) close to the target and then feeding the coil with a current, typically of a pulsed waveform, produced by discharging the energy of, e.g., a charged capacitor, whereby an electric field is induced in the tissue in accordance with Maxwell's equations. If the structure of the object and the conductivities of its different parts (such as the skull and the brain) are known, the electric field induced by the current passing in the coil can be computed as a function of the position coordinates of the object. In the art are also known other methods suitable for positioning one or more coils about the head and then feeding an electric current to the coil or coils so that an electric field with a precisely defined electric field is resultingly induced in the object.

One of the problems hampering prior-art methods and equipment in certain applications is that the effects of brain stimulation can be recorded without artefacts only peripherally by measuring, e.g., muscular responses or observing the behavioral response of the tested person. In fact, only qualitative results can be obtained from evoked-response EEG results measured and interpreted by conventional techniques in conjunction with electromagnetic stimulation.

A further problem of prior-art techniques and equipment is that the cortical activity evoked by electromagnetic stimulation cannot be localized.

Still another problem of certain methods and equipment of the prior art is that the effect of cortical stimulation can be measured by EEG techniques only after tens or hundreds of milliseconds after the stimulus pulse.

The present invention is based on 1) stimulating selected areas of the cerebral cortex by magnetic or electrical means,
2) measuring the electrical activation of the brain as a function of time using multichannel equipment such as EEG or MEG, and
3) localizing with the help of multichannel techniques the originating loci of signals detected as a result of the electrical activation of the brain, or alternatively, focusing the sensitivity maximum of said electrical multichannel measurement on a certain location or locations.

In the context of the present invention, the term localization refers to a mono- or multi-dipole localization or to the computation of minimum-norm estimates or other current distributions estimating the location of diffuse source current patterns.

If a localization listed in item 3) above indicates that the brain is activated in an area B after the stimulation of a brain area A, it is obvious that a nerve cell connection exists from area A to area B. The magnitude of the stimulated activity, which can be determined in an approximating manner during localization, is a measure of the reactivity of area B for the stimulation of area A. In the case that the areas A and B are separate (section of areas A and B being essentially zero), the phenomenon is called secondary reactivity, whereby the evoked response in area B occurs with a distinct delay after the onset of the stimulus, since the velocities of conduction and intersynaptic delays in the transmission from one nerve cell to another are relatively slow phenomena. Typically the delays between different cortical areas vary from a few milliseconds to tens of milliseconds depending on the interarea distances and the type of cortical connections whether direct or formed by a chain of several nerve cells. If the areas A and B are practically the same area or B is included in A, the method gives the reactivity of the stimulated area to the stimulus. Then, the measured variable is called the primary reactivity.

In addition to primary and secondary reactivities, other changes in the spontaneous activity of the brain due to stimulation may be detected. When a conventional technique is used based on applying a nervous stimulus such as a sound on the test person, the stimulated response is generally called event-dependent desynchronization, wherein the strong brain waves resulting from the synchronous excitations of nerve cells in a rest state of the brain are attenuated due to the applied stimulus. Also other changes can be seen different from those of desynchronization. For instance, the frequency of rhythmic activity in the brain may vary or the position distribution of the activity may change. In the context of the present invention, the sensitivity of spontaneous activity to change can be called the reactivity of the spontaneous activity. By measuring the primary, secondary and spontaneous-activity reactivities from different areas of the brain, important information can be obtained on the status of human cortex and associated parts of the brain system during psychological tests, stress, diseases or drug administration.

In certain procedures, the arrangement according to the present invention can be used to examine the recovery rate of the cortex from applied pulses. Such a test session can be arranged as follows:

1) a stimulus pulse is applied on area A,
2) another stimulus pulse is applied on such an area B that activates the cortical area A in a manner suitable for recording by EEG equipment,
3) items 1 and 2 are repeated using different interpulse delays and simultaneously recording the EEG response of area A as a function of said interpulse delay duration. This technique gives information on the persistence of the stimulation caused by the pulse applied on area A. When desired, the stimulus used in step 2 may alternatively be applied as a sensory stimulus.

The invention offers significant benefits.

The method and apparatus according to the invention are capable of combining the flexible and accurate focusing and timing of multichannel magnetic-field stimulation with the response localization technique of multichannel EEG. Hence, an entirely novel approach to brain research is achieved. By virtue of the novel method, brain function can be mapped in a rapid and systematic manner by stimulating different areas of the brain and simultaneously recording multichannel EEG signals, thus localizing evoked responses for different interpulse delay durations from the instant of the pulsed stimulus.

In the following, the invention will be examined in greater detail by making reference to the appended drawings illustrating a preferred embodiment of the invention, in which drawings FIG. 1a shows a prior-art stimulation arrangement in a side view;

FIG. 1b shows a diagram illustrating a typical case of the distribution of the electric field induced by means of the arrangement shown in FIG. 1a;

Figure 1A:
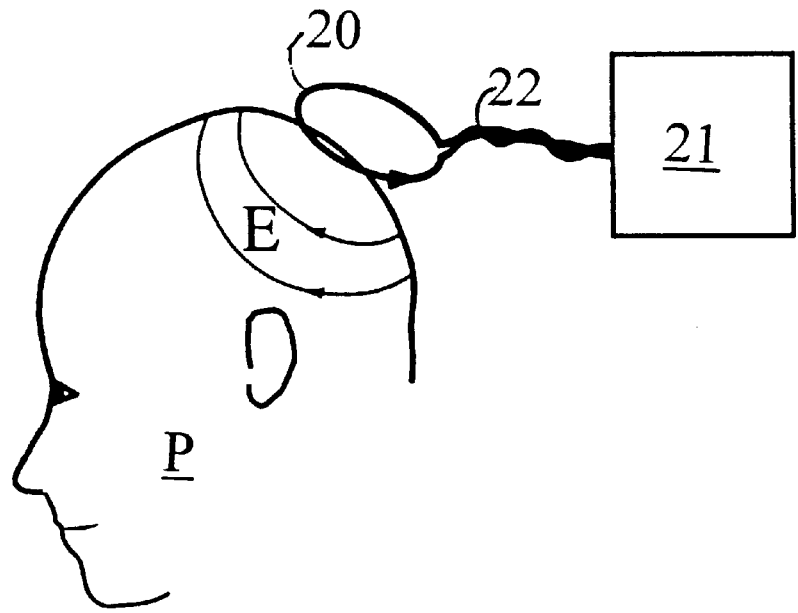

Referring to FIG. 1a, the conventional technique illustrated in the diagram is based on using a single current coil 20 to generate a changing magnetic field in an area P, whereby an electric field E is induced in the object. The coil 20 receiving its current pulse from a current source 21 via a cable 22 must be placed close to the area P.

Figure 1B:
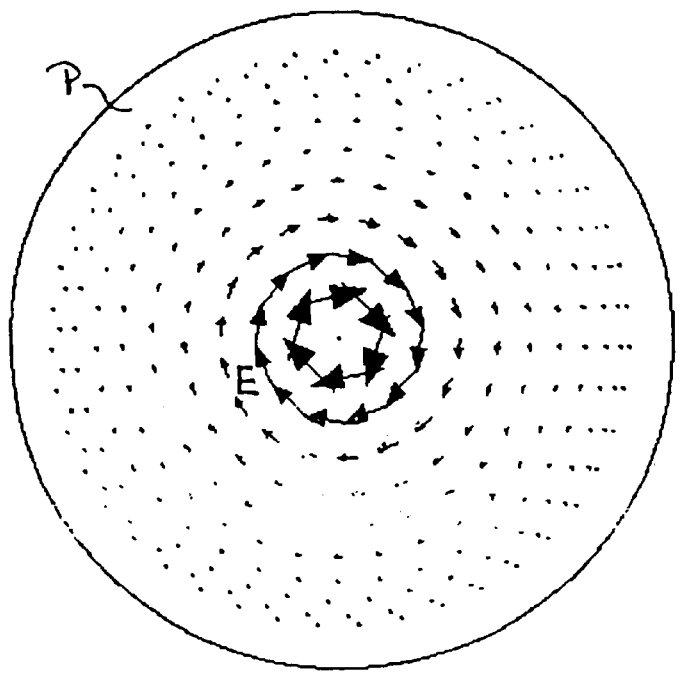

In FIG. 1b is shown the distribution of the induced electric field E as a function of location in the prior-art measurement configuration of FIG. 1a when the coil 20 is placed at a distance of 10 mm from the surface of a spherical conducting test object having a radius of 90 mm and the field distribution is computed for a spherical surface assumed to be 15 mm under the outer surface of the conducting object. The length of each arrow is drawn proportional to the magnitude of electric field at the center of the arrow with the tip of the arrow pointed in the direction of the field. The field distribution shown is plotted having the coil located above the center point of the diagram.

Figure 2:
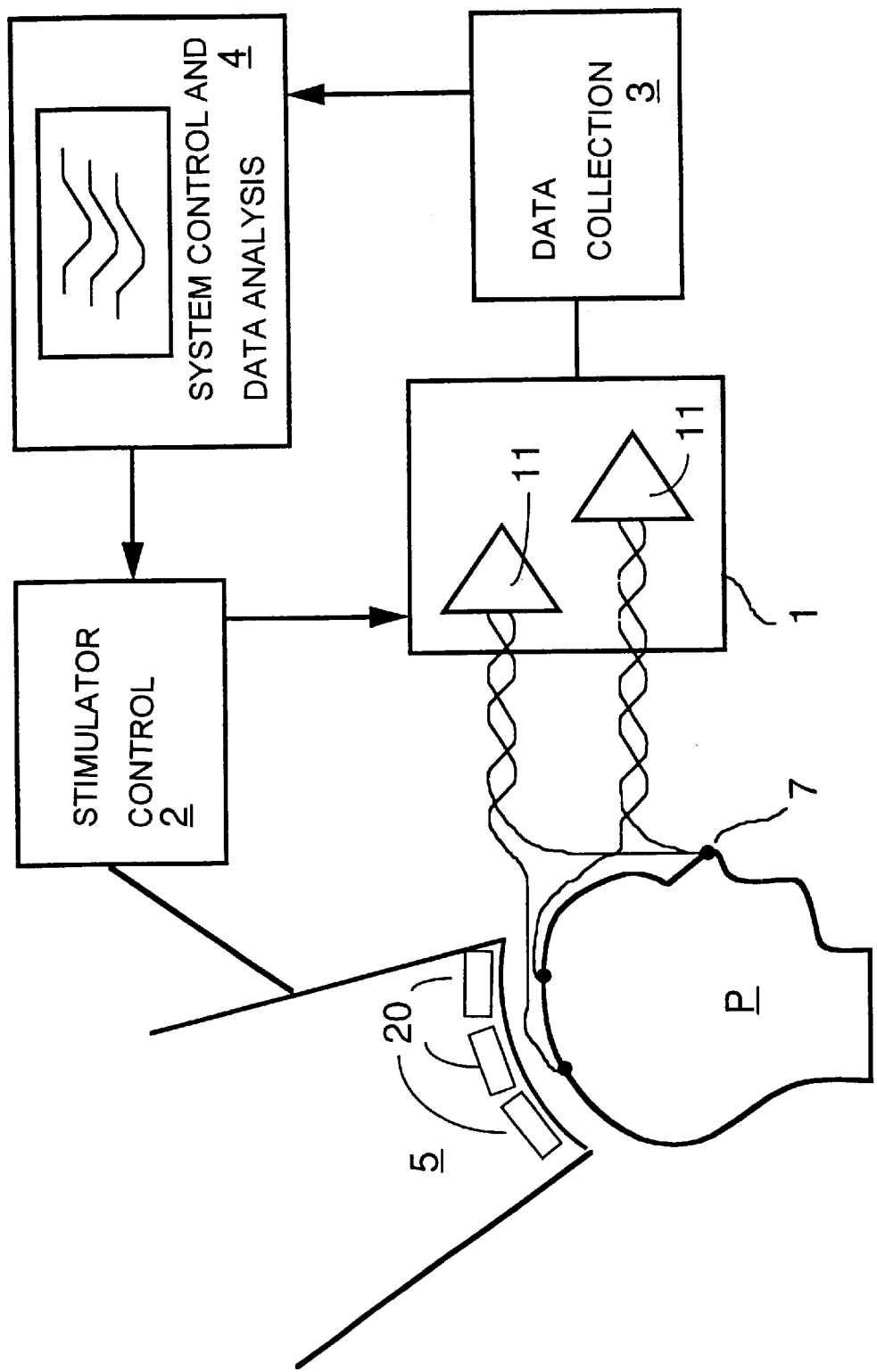
FIG. 2 shows a block diagram of a measurement configuration according to the invention.

As shown in FIG. 2, the measurements are performed by attaching electrodes 6 to the head of the test person P, whereby the number of the electrodes must typically be at least 6 in order to accomplish a reliable recording of responses evoked in the brain tissues. Respectively, the minimum total number of the electrodes for simultaneous recording of both hemispheres is 12. Since this minimum number of electrodes is sufficient for localization only when the activity to be localized is in a very favourable area and orientation with respect to the electrodes, practical applications are preferably provided with a greater number of measurement channels; for instance, the electrodes may be formed into a matrix comprising advantageously from 32 to 128 electrodes. While the measurement accuracy is improved with the higher number of electrodes, generally a very marginal benefit is gained by using more than 128 electrodes. The reference, or counter electrode 7 is attached to a suitable place on the test object, typically on the nose, mastoid region or scalp of the test person P. With the help of the coils 20 of the stimulator system 5, a stimulating signal is applied in the above-described manner and the signals obtained from the electrodes 6 are recorded by means of amplifiers 11 of the EEG equipment 1. With the help of a control unit 2, the signals of the stimulating coils 20 and the output signals of the measurement equipment 1 are synchronized with each other for the determination of the evoked-response pattern. The evoked-response pattern is formed from the information gathered by the data collection unit 3 by means of the control and analysis unit 4 of the measurement system. The evoked-response brain activity occurring synchronized with the applied stimulus can be separated from other activity using such methods as averaging of EEG signals recorded subsequent to a plurality of stimulus pulses or computation of cross-correlations between the recorded EEG signals and the timing signals associated with the applied magnetic stimulus pulses.

Figure 3:
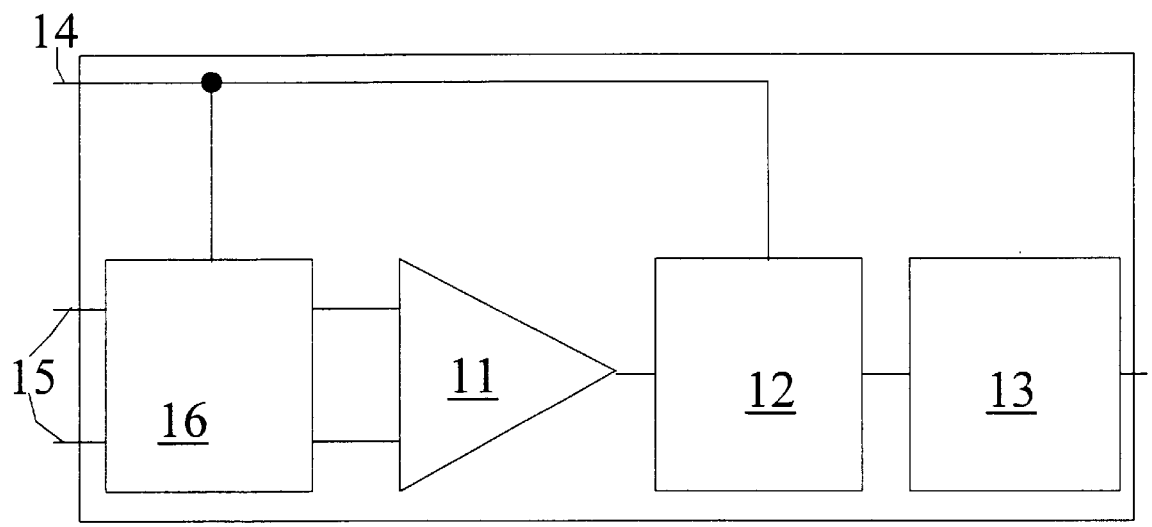
FIG. 3 shows a block diagram of the EEG recorder used in the measurement configuration according to the invention.

Referring to FIG. 3, the EEG equipment shown therein comprises a differential amplifier 11 to which cables 15 from the electrodes are connected via transient voltage limiters 16. To assure patient safety, the signal-conditioning part having immediate electrical contact with the patient is electrically isolated from the rest of the equipment typically by means of transferring the measurement signals from the patient to the measurement equipment by optical or electromagnetic means such as an optoisolator or transformer, for instance. While the circuit blocks normally placed close to the patient comprise at least the elements 15, 16 and some sections of block 11, even the entire circuitry of FIG. 3 may be included. After amplification, the signal is filtered by a low-pass filter 13 with a cut-off frequency below 1000 Hz typical.

Figure 4:
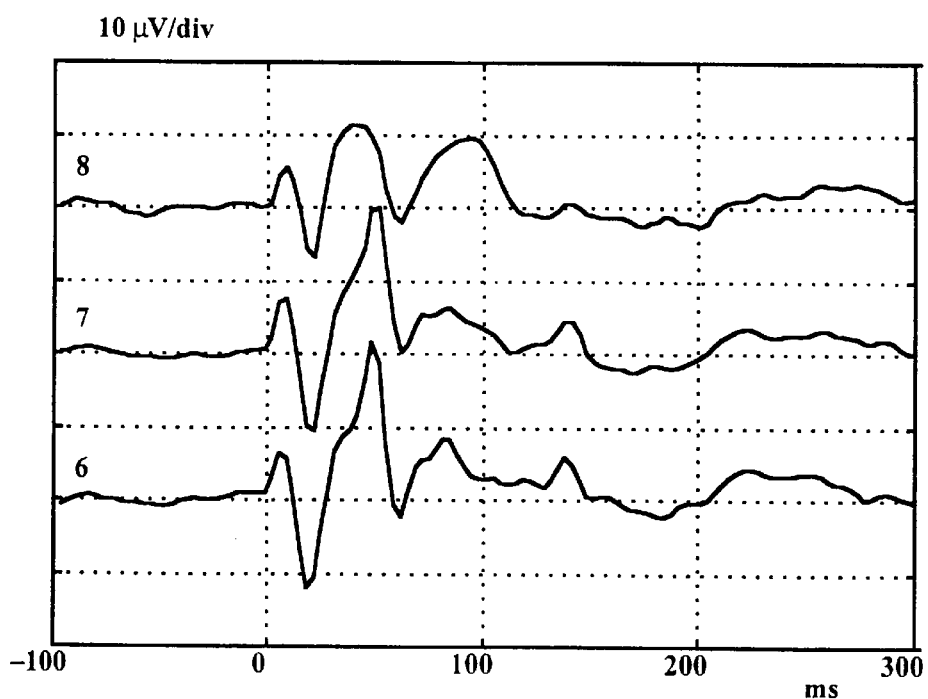
FIG. 4 shows a plot of the multichannel EEG recorder output signals in the measurement configuration according to the invention.

In FIG. 4 are plotted EEG signals measured from the brain obtained by applying a magnetic stimulus pulse at instant t=0 in the brain of the test person and then averaging the results of 300 these evoked-response measurement cycles. Typically, a test session is carried out applying 10–1000 pulses with the averaging of their evoked-response recordings. In practical applications, the number of pulses applied is generally in the range 30–300.

To minimize the interference of the applied stimulus pulse, certain special requirements are set on the EEG equipment used in conjunction with stimulator equipment. The degree of interference can be reduced by shaping the spectrum and wave shape of the stimulus pulse such as to be free from frequency components falling within the desirable passband of the evoked-response EEG recording equipment, advantageously covering 0–1000 Hz frequency range.

Additionally, interference reduction can be achieved by minimizing the mutual impedance between the conductor loops formed by the EEG cables and the test object and the coils of the magnetic stimulator.

Capacitively coupled interference may be reduced by erecting a grounded electrical shield about the magnetic stimulator and/or the EEG equipment used in the measurement.

In the diagrams, the interference reduction means 16 and 12 either eliminate the stimulus artefact directly or perform conditioning of the interference-causing signal such that the artefact component imposed on the measurement signal due to the limited response speed of the amplifier circuits and filters has a predictable form, thus permitting elimination of the artefact by subtraction.

The functions of blocks 12 and 13 may also be implemented by computational means subsequent to the analog-to-digital conversion of the signals.

The block 16 may comprise a low-pass filter designed to attenuate the frequency components of the stimulus artefact. Additionally, the block may include active or passive transient voltage limiters. The block 12 includes advantageously a sample and hold circuit capable of clamping the amplifier output signal for the duration of the stimulus pulse to the level just preceding the application of the stimulus pulse. The use of a hold circuit facilitates free location of EEG electrodes on the surface of the head without any risk of interference from the stimulus pulses during measurement. The block 16 is advantageously designed to have a high input impedance also during the application of the stimulus pulse. Herein, the input impedance $Z_{in}$ is typically kept higher than 10 kohm.

In a preferred embodiment of the apparatus, the interference-eliminating circuits avail of a separate synchronizing signal issued in advance to the stimulus pulse. Alternatively, interference elimination can be implemented based on timing information extracted from the measurement signal.

An approach to interference reduction is based on measuring the artefacts caused by the stimulus pulse using a pulse amplitude smaller than that required for the minimal response and the artefacts thus identified are subtracted from responses measured using a pulse amplitude larger than that of the minimal response. Obviously, the artefact measured first must be weighted by the ratio of the stimulus pulse amplitudes prior to said subtraction in order, thus permitting elimination by subtraction of the artefact directly coupled from the stimulus pulse.

An advantageous approach to the measurement of EEG signals in conjunction with electromagnetic stimulation is to use EEG amplifiers with a special design and circuitry capable of producing during the stimulus pulse a constant-waveform signal which is independent from the stimulus pulse amplitude and waveform. This property can be implemented in one of the following manners:

a) controlling the amplifier with an external input signal indicating the application instant of the stimulus pulse so as to force the amplifier into a known state for the duration of the stimulus pulse, b) identifying the stimulus pulse from the input signal with the help of an internal logic circuitry of the amplifier and then forcing the amplifier into a known state for the duration of the stimulus pulse, or c) using such a design and construction of the amplifier that permits one of its amplifying stages to saturate as soon as the input signal level exceeds that occurring in normal EEG recording.

In the approach based on EEG amplifier designs capable of producing a constant-waveform output signal during the stimulus pulse, the artefact components can be measured using a stimulus pulse amplitude smaller than the minimal response level and then subtracted from the actual responses measured using a stimulus pulse amplitude higher than required for the minimal response. However, this technique does not need the above-mentioned weighting, because the electronically conditioned input signal during the stimulus is independent from the amplitude of the stimulus pulse.

In certain preferred embodiments, the design and construction of the EEG amplifier is made with a passband so wide (advantageously extending above 1000 Hz) and a recovery so fast (advantageously faster than 1–2 milliseconds) from saturation that the artefact caused by the stimulus pulse can decay in the amplifier stages prior to the activation of the measured responses.

In still other preferred embodiments, the input signal is converted into digital format and subjected before low-pass filtration to the above-mentioned digital conditioning of the signal during the stimulus pulse. Here, the artefact subtraction technique already described above can be used.

In lieu of an EEG recorder, the arrangement according to the invention may also be implemented using multichannel MEG equipment. However, this method requires the use of modern interference suppression techniques such as effective magnetic shielding or temporally gated measurement.

In one suitable embodiment, the flux transformers of the MEG sensors are provided with a superconductive loop comprising 1) a conductive loop called the pickup coil, which is placed in magnetic field being measured, 2) a conductive loop called the signal coil, which inductively couples the signal to be measured to the SQUID sensor, and 3) a cable such as a twisted pair conductor connecting the pickup coil with the signal coil.

When the external magnetic field changes, a current is induced in the flux transformer that further generates in the signal coil a magnetic field which is coupled to the SQUID. In an embodiment according to the invention, the SQUID and the signal coil are outdistanced from the electromagnetic stimulator or placed inside a superconductive shield, whereby the SQUID cannot be directly disturbed by the stimulus pulse. Interference transmitted via the flux transformer to the SQUID is advantageously eliminated by short-circuiting (shunting) the pickup coil for the duration of the stimulus pulse. Such short-circuiting can be accomplished by mechanical means or using a superconductive switch which can be opened by thermal, optical or electronic means. Shunting may also be implemented by switching a capacitor over the conductors of the connecting cable, whereby high-frequency interference transmitted toward to the SQUID will be attenuated.

Furthermore, the apparatus according to the invention may be designed for interactive control by the operator of the equipment permitting real-time adjustment of the focus coordinates, field direction and amplitude of the stimulating electromagnetic field on the basis of information obtained from a computer terminal screen or other devices such as loudspeakers on the change of EEG recorder signals. Alternatively, the system parameters may be varied automatically by a preset control algorithm implemented with the help of a computer. Such a real-time control permits, e.g., altering the stimulus amplitude, focus or repetition rate when the recorded EEG signal indicates an activity critical in terms of safety regulations or the comfort of the test person or patient. In a preferred embodiment, the multichannel EEG signal is processed into weighted sums of the signals obtained from the different channels such that the composite signal thus formed is sensitive to the electrical activity of the selected brain area.

A preferred embodiment of the invention is characterized in that a rapidly changing magnetic field is inflicted on the test object by means of a plurality of coils placed outside the object, whereby each of the coils is fed with a preset and controlled current so that the generated magnetic field and/or the induced electric field have an operator-controlled pattern and distribution in the object. Using a mouse or other pointing device, the operator can select the area to be stimulated in the object from an anatomical picture displayed on a graphic device such as a computer terminal screen.

Another preferred embodiment of the invention is characterized in that a single-channel stimulator is used capable of controlling the position of the stimulator with respect to the test object's head, advantageously using a mechanism permitting accurate stereotactic positioning of the stimulator.

A still another preferred embodiment of the invention has the EEG electrodes or their attachment fixtures designed into an integral part of the multichannel electromagnetic stimulator construction. In a still further another embodiment, the inside surface of the magnetic stimulator unit to be placed in intimate contact with the head is shaped so as not to prevent the electrodes attached to the scalp from interfering with the adaptation of the stimulator apparatus close to the scalp. For this purpose, the surface of the coil fixture of the apparatus can be provided with recesses.

A third preferred embodiment of the invention is characterized in that the stimulator used is an electrical stimulator.

A fourth preferred embodiment of the invention is characterized in that in the first step, an accurately focused stimulus is applied to different points of area A (whose dimensions are selected to be compatible with the resolution of the EEG locationing system) in order to scan the area B with the help of EEG techniques, simultaneously looking for the best point C for activating area B, whereafter the stimulus is focused precisely on different points of area B with the goal of finding a point D which causes maximum activation within the area A. Resultingly, the points C and D will be localized with the resolution of the stimulating system which generally is better than that of the recording system used for localizing the points of response. In certain instances, it is thus possible to infer that a stronger neural connection exists between the points C and D than between the neighbouring areas.

Figure 5A:
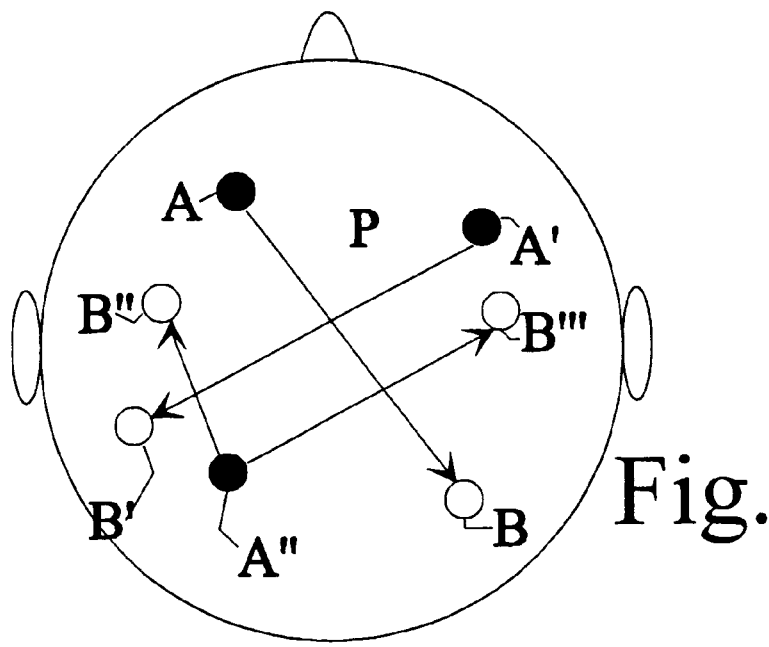
FIGS. 5a and 5b show alternative mapping techniques of brain activity based on the response recordings of the measurement methods according to the invention.

If the localization result obtained by virtue of the invention shows the brain to be activated in the area B after the brain area A has been stimulated, it is obvious that a nerve cell connection exists from area A to area B. By stimulating with the method of the invention in an alternative manner the areas A, A', A", etc., and subsequently recording the activities of areas B, B', B", etc., the different regions and connections of the brain can be scanned, whereby a computer may be utilized to extract and display the connection maps of different brain areas as shown in FIG. 5a.

Figure 5B:
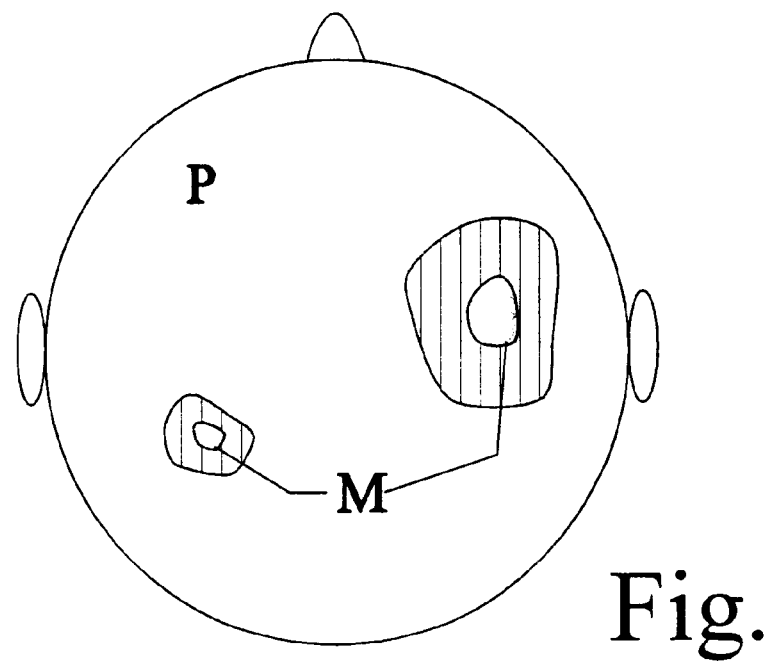

When B and A are practically the same area or B is included in A, the reactivity of the stimulated area for the stimulus applied on latter area can be determined as shown in FIG. 5b. This can be called the primary activity. In a preferred embodiment of the invention, the reactivity maps of FIG. 5b can be plotted by alternate stimulation of different points of the brain with simultaneous recording of the activation of the area evoked by the stimulation, after which the amplitudes of evoked responses are plotted into isocontour maps. Areas M of the diagram denote the areas of maximal response.

Correspondingly, EEG can be used for recording sensory-stimulus-evoked responses on certain brain areas under simultaneous electromagnetic stimulation, whereby changes in EEG responses under the stimulus can be assessed.

The information provided by the stimulation reaction and connection maps and the changes of sensory-stimulus-evoked responses under electromagnetic stimulation can be used in the on-line or off-line planning of stimulation applied to the test person. For instance, if the effect of a drug on the function of nerve cell connections between the hemispheres is to be tested, an interhemisphere connection map is advantageously recorded prior to the test in order to select a specific connection to be examined during the test session. Respectively, the reactivity map can be utilized for selecting a desired area of maximal or minimal response for closer examinations.

The invention makes it possible to perform on-line monitoring of reactivity changes during different treatments or therapies, whereby the efficacy of the therapy can be assessed in real time. The possible forms of therapy considered herein include radiation therapy, surgical operations, drug treatment and any other type of therapy utilizing psychological or electromagnetic stimulation.

In certain applications, the stimulus may comprise a series of multiple electromagnetic stimulus pulses. Certain applications may be advantageously carried out using a series of 2–30 pulses applied with 5–100 ms interpulse intervals. Using computerized control, some applications can utilize a preprogrammed criterium for real-time control of the stimulus pulse series, based on the EEG signal measured in conjunction with the application of such a stimulus pulse series.

The invention also facilitates the determination of the location and/or activation site of the stimulus pulse by means of multichannel EEG measurement. Furthermore, the invention improves the repeatability of measurements by virtue of the correct focusing of the stimulus. This is an advantageous possibility particularly in conjunction with the use of single-channel stimulus equipment having large external dimensions of the stimulator coil, and resultingly, posing great difficulties in accurate determination of the focus of the stimulus.

What is claimed is:

1. A method of examining and mapping the reactivity of and connections between different cortical areas of a subject, said method comprising:

inducing an electromagnetic stimulus pulse in the interior of the subject's head, measuring a multichannel response signal representing electromagnetic activity generated by the subject's brain in response to the electromagnetic stimulus pulse by multichannel electrical means, stabilizing or clamping said multichannel response signal during at least one stage of the measurement for the duration of the stimulus pulse in order to minimize disturbance artefacts in said multichannel response signal caused by application of the stimulus pulse, forming a visualization of activity changes in the measured signals, and localizing the activity generating the measured electromagnetic field to the respective areas of the head, or alternatively focusing the sensitivity pattern of the multichannel activity measurement to a desired point.

2. A method according to claim 1, including measuring said electromagnetic field by EEG techniques.

3. A method according to claim 1, including measuring said electromagnetic field by MEG techniques.

4. A method according to claim 1, including measuring said electromagnetic field by EEG and MEG techniques.

5. A method according to claim 1, including adjusting the magnitude of the magnetic stimulation during a test session according to the electromagnetic response obtained in the measurement.

6. A method according to claim 5, comprising adjusting the magnitude of the stimulation automatically.

7. A method according to claim 1, comprising monitoring said responses and, in the case that the measured signals indicate characteristic features of an onsetting epileptic fit or other abnormal activity, limiting the magnitude of the stimulation.

8. A method according to claim 1, comprising measuring the artefact components using a stimulus pulse amplitude smaller than that required for a minimal response and subtracting the artefacts thus identified from responses measured using a stimulus pulse amplitude larger than that of the minimal response, and weighting the artefact measured in the first step by the ratio of the stimulus pulse amplitudes prior to said subtraction in order to permit elimination by subtraction of the artefact directly coupled from the stimulus pulse.

9. A method according to claim 1, including using a computer for controlling the focusing of the stimulation in order to scan an area of the brain, whereby the computer compiles and displays reactivity and connection maps.

10. A method according to claim 1, comprising measuring evoked-response signals related to sensory stimuli, stimulating an area of the brain by electromagnetic fields and using EEG for measuring changes of EEG signals due to said sensory stimuli under said electromagnetic stimulation.

11. A method according to claim 1, comprising using the reactivity test for improving safety.

12. A method according to claim 1, including assessing on-line effects of applied therapy during a therapy session from recorded changes in brain reactivity.

13. A method according to claim 1, including on-line or off-line planning of the stimulation method to be applied on the subject on the basis of reactivity and connection maps produced with the help of the stimulator apparatus.

14. A method according to claim 1, wherein the multichannel electrical means includes an amplifier for receiving the multichannel response signal and generating an output signal, and the method includes controlling the amplifier with an external control signal that forces the amplifier into a predetermined state for the duration of the stimulus pulse.

15. A method according to claim 1, wherein the multichannel electrical means includes an amplifier for receiving the multichannel response signal and generating an output signal, the amplifier includes logic circuitry for identifying the stimulus pulse, and the method includes forcing the amplifier into a predetermined state for the duration of the stimulus pulse.

16. A method according to claim 1, wherein the multichannel electrical means includes an amplifier for receiving the multichannel response signal and generating an output signal, the amplifier includes a stage that saturates in the event that the input signal level exceeds a predetermined threshold level.

17. An apparatus for examining and mapping the reactivity of and connections between different cortical areas of a subject, said apparatus comprising:

a stimulating means for inducing an electromagnetic stimulus pulse in the interior of the subject's head, and a multichannel electrical measurement means for recording the electromagnetic field generated around the skull, said multichannel electrical measurement means including a clamping or stabilizing means for clamping or stabilizing the input signal of the multichannel electrical measurement means during at least one stage of the measurement for the duration of the stimulus pulse in order to minimize disturbance artefacts caused by application of the stimulus pulse, an evoked-response analysis means for forming a graphic or numeric visualization of the signals measured by the multichannel electrical measurement means, and a localizing means for localizing the areas of the head related to the activity generating the measured electromagnetic field.

18. An apparatus according to claim 17, wherein the electrode conductors are made over their partial or entire length from a material of relatively low conductivity.

19. An apparatus according to claim 17, wherein the multichannel electrical measurement means includes an EEG amplifier having so wide a passband, advantageously extending above 1000 Hz, and so fast a recovery (advantageously within 1–2 ms) from saturation that the artefact component caused by the stimulus pulse can decay before the responses to be measured are activated.

20. A method for examining and mapping the reactivity of and connections between different cortical areas of a subject using apparatus that comprises a stimulating means for inducing an electromagnetic stimulus pulse in the interior of the subject's head and a multichannel electrical measurement means for recording the electromagnetic field generated around the skull, wherein the method comprises clamping or stabilizing the input signal of the multichannel electrical measurement means during at least one stage of the measurement for the duration of the stimulus pulse in order to minimize disturbance artefacts caused by application of the stimulus pulse, processing the signals measured by the multichannel electrical measurement means to form a visualization of changes in electromagnetic activity, and localizing the areas of the head related to the activity generating the measured electromagnetic field.

* * * * *